US010570366B2

(12) United States Patent
Matsuura et al.

(10) Patent No.: US 10,570,366 B2
(45) Date of Patent: Feb. 25, 2020

(54) LACTIC ACID BACTERIUM HAVING IGA PRODUCTION PROMOTING ACTIVITY, AND USE THEREOF

(71) Applicant: YAMADA BEE COMPANY, INC., Okayama (JP)

(72) Inventors: Daisuke Matsuura, Okayama (JP); Takashi Asama, Okayama (JP); Hironori Motoki, Okayama (JP); Tomoki Tatefuji, Okayama (JP); Ken Hashimoto, Okayama (JP)

(73) Assignee: Yamada Bee Company Inc., Tomata-gun, Okayama ( * ) Notice: Subject to any disclaimer, the term of this patent is extended or adjusted under 35 U.S.C. 154(b) by 0 days.

(21) Appl. No.: 15/835,126

(22) Filed: Dec. 7, 2017

(65) Prior Publication Data

US 2018/0112176 A1 Apr. 26, 2018

Related U.S. Application Data

(63) Continuation of application No. 14/369,625, filed as application No. PCT/JP2012/083523 on Dec. 25, 2012, now Pat. No. 9,856,451.

(30) Foreign Application Priority Data

Dec. 28, 2011 (JP) ................................ 2011-289314

(51) Int. Cl.
*C12N 1/20* (2006.01)
*A61Q 19/08* (2006.01)
*A61K 8/99* (2017.01)
*A61K 8/02* (2006.01)
*A23L 33/135* (2016.01)
*C12R 1/225* (2006.01)
*A61K 35/747* (2015.01)

(52) U.S. Cl.
CPC .............. *C12N 1/20* (2013.01); *A23L 33/135* (2016.08); *A61K 8/0212* (2013.01); *A61K 8/99* (2013.01); *A61Q 19/08* (2013.01); *C12R 1/225* (2013.01); *A61K 35/747* (2013.01)

(58) Field of Classification Search
None
See application file for complete search history.

(56) References Cited

U.S. PATENT DOCUMENTS

| | | | |
|---|---|---|---|
| 5,580,297 A | 12/1996 | Bengsch | |
| 2003/0157079 A1 | 8/2003 | Kato et al. | |
| 2008/0311097 A1* | 12/2008 | Israelsen | A61K 31/685 424/93.44 |
| 2011/0104134 A1 | 5/2011 | Ihara et al. | |
| 2011/0182859 A1* | 7/2011 | Hyde | A61K 35/74 424/93.2 |

FOREIGN PATENT DOCUMENTS

| | | |
|---|---|---|
| JP | H05-064555 A | 3/1993 |
| JP | H07-507459 A | 8/1995 |
| JP | H08-143462 A | 6/1996 |
| JP | H11-507934 A | 7/1999 |
| JP | 2002-241289 A | 8/2002 |
| JP | 2004-502633 A | 1/2004 |
| JP | 2007-070249 A | 3/2007 |
| JP | 2007-269737 A | 10/2007 |
| JP | 2008179630 A | 8/2008 |
| JP | 2008-201708 A | 9/2008 |
| JP | 2009-509981 A | 3/2009 |
| JP | 2009-511471 A | 3/2009 |
| JP | 2010-057395 A | 3/2010 |
| JP | 2010-525809 A | 7/2010 |
| JP | 2010-285421 A | 12/2010 |
| WO | WO 1997/00688 | 1/1997 |
| WO | 2000/041707 A2 | 7/2000 |
| WO | 2002/016554 A | 2/2002 |
| WO | 2004/076615 A2 | 9/2004 |
| WO | 2007/036230 A1 | 4/2007 |
| WO | 2007/040446 A1 | 4/2007 |
| WO | 2008/136730 A1 | 11/2008 |
| WO | WO 2010/001509 | 1/2010 |
| WO | 2013/099883 | 7/2013 |

OTHER PUBLICATIONS

Malin et al., "Promotion of IgA Immune Response in Patients with Crohn's Disease by Oral Bacteriotherapy with Lactobacillus GG," Annals of Nutrition and Metabolism, 1996, vol. 40, pp. 137-145.
Ohkusa, "Effect of Probiotic Therapy on Inflammatory Bowel Disease," Journal of Intestinal Microbiology, 2009, vol. 23, pp. 193-201.
Gupta et al., "Is lactobacillus GG Helpful in Children with Crohn's Disease? Results of a Preliminary, Open-Label Study," Journal of Pediatric Gastroenterology and Nutrition, 2000, vol. 31, No. 4, pp. 453-457.
Harata et al., "Intranasal administration of Lactobacillus Rhamnosus GG protects mice from H1N1 influenza virus infrction by regulating respiratory immune responses," Letters in Applied Microbiology, 2010, vol. 50, pp. 597-602.

(Continued)

Primary Examiner — David W Berke-Schlessel
(74) Attorney, Agent, or Firm — Fish & Richardson P.C.

(57) ABSTRACT

Disclosed are: a lactic acid bacterium belonging to *Lactobacillus kunkeei*, the bacterium having a higher IgA production inducing activity than that of *Lactobacillus* strain GG (ATCC53103), and a lower mitogenic activity and a lower IL-2 production inducing activity than those of *Listeria* strain EGD; and a food composition, a pharmaceutical composition, a cosmetic composition, an immunostimulant for preventing the infection by pathogens or viruses that invade through the respiratory or esophageal mucosa, and an intestinal immunostimulant for preventing or alleviating food poisoning, each of which contains the lactic acid bacterium or treated cells of the lactic acid bacterium.

7 Claims, 7 Drawing Sheets
Specification includes a Sequence Listing.

(56) References Cited

OTHER PUBLICATIONS

Niessner et al., "Altered Th1/Th2 cytokine profiles in the intestinal mucosa of patients with inflammatory bowel disease as assessed by quantitative reversed transcribed polymerase chain reaction (RT-PCR)," Clinical and Experimental Immunology, 1995, vol. 101, pp. 428-435.

Edwards et al., "*Lactobacillus kunkeei* sp. Nov.: a spoilage organism associated with grape juice fermentations," Journal of Applied Microbiology, 1998, vol. 84, pp. 698-702.

Endo et al., "Isolation and characterization of fructophilic lactic acid bacteria from fructose-rich niches," Systematic and Applied Microbiology, 2009, vol. 32, pp. 593-600.

Olofsson, Tobias C; Vasquez, Alejandra; "Detection and Identification of a Novel Lactic Acid Bacterial Flora Within the Honey Stomach of the Honeybee *Apis mellifera*" Current Microbiology, 57, 356-363, 2008.

Asama et al., "Lactobacillus kunkeei YB38 from honeybee products enhances IgA production in healthy adults," J Applied Microbiol, 119, 818-826, 2015.

Krushna, NSA; et al; "Honey as a natural preservative of milk" Indian Journal of Experimental Biology, 45, 459-464, 2007.

Munehiro Oda and Yu Kuwata, "Application of Intestinal Foods and Probiotics," Vitamins (Japan), 78(11):565-567, 2004 (with partial translation).

Hachimura, "Immune-Modulation by Lactic Acid Bacteria," Japanese Journal of Acid Bacteria, 2007, 18(2):54-57 (with English Translation).

JP Office Action in Japanese Appln. No. 2017-145866, dated Jul. 17, 2019, 7 pages (with English translation).

Kaufmann et al., "Interleukin 2 Induction in Lyt 1+23-T Cells from Listeria Monocytogenes-Immune Mice," Infection and Immunity, 1982, 37(3):1292-1294.

Koga et al., "Induction by Killed Listeria Monocytogenes of effector T Cells Mediating Delayed-Type hypersensitivity but not Protection in Mice," Immunology, 1987, 62:241-248.

Takeda et al., "Mitogenic Activity of Whole Cells and Cell Wall Components of Lactobacillus Acidophilus Group Lactic Acid Bacteria on Murine Spleen and Peyer's Patch Cells," Milchewissenschaft, 1997, 52(1):21-25.

Takeda et al., "Mitogenic Activity of Whole Cells and Cell Wall Components of Lactobacillus Acidophilus Group Lactic Acid Bacteria on Murine Spleen and Peyer's Patch Cells," Milchwissenschaft 1997, 52(1):21-25.

JP Office Action in Japanese Appln. No. 2017-145866, dated Jul. 23, 2019, 7 pages. (with English translation).

\* cited by examiner (N.D.: Non-detectable)

SEQUENCE LISTING

<160> NUMBER OF SEQ ID NOS: 3

<210> SEQ ID NO 1
<211> LENGTH: 1499

```
<212> TYPE: DNA
<213> ORGANISM: Lactobacillus kunkeei

<400> SEQUENCE: 1
gacgaacgct ggcggcgtgc ctaatacatg caagtcgaac gagctctccc aaattgattt      60
tatgcttgca taaatgattt ttggattcgg agcgagtggc gaactggtga gtaacacgtg     120
ggtaacctgc cccgaagcgg gggataacat ttggaaacaa gtgctaatac cgcataatta     180 gttgaaccg catggttcca acttgaaaga tggctctgct atcactttgg gatggacccg      240
cgccgtatta gttagttggt gagataaaag cccaccaaga cgatgatacg tagccgacct     300
gagagggtaa tcggccacat tgggactgag acacggccca gactcctacg ggaggcagca     360
gtagggaatc ttccacaatg gacgaaagtc tgatggagca acgccgcgtg agtgatgaag     420
gttttcggat cgtaaaactc tgttgttaaa gaagaacaag tgttagagta actgttaaca     480
ctttgacggt atttaaccag aaagccacgg ctaactacgt gccagcagcc gcggtaatac     540
gtaggtggca agcgttgtcc ggatttattg ggcgtaaagc gagcgcaggc ggttttgtaa     600
gtctgctgtg aaagccctca gctcaactga ggaagtgcag tggaaactac aaaacttgag     660
tacagaagag gaaagtggaa ctccatgtgt agcggtgaaa tgcgtagata tatggaagaa     720
caccagtggc gaaggcggct ttctggtctg ttactgacgc tgaggctcga agcatgggt      780 agcgaacagg attagatacc ctggtagtcc atgccgtaaa cgatgaatac taggtgttgg     840
agggtttccg cccttcagtg ccgcagctaa cgcattaagt attcgcctg gggagtacga      900 ccgcaaggtt gaaactcaaa ggaattgacg ggggcccgca caagtggtgg agcatgtggt     960
ttaattcgat gctacgcgaa gaaccttacc agctcttgac atcttctgcc aacccaagag    1020
attgggcgtt ccctttcgggg acagaatgac aggtggtgca tggttgtcgt cagctcgtgt   1080
cgtgagatgt tgggttaagt cccgcaacga gcgcaaccct tattattagt tgccagcatt    1140
tagttgggca ctctagtgag actgccggtg ataaaccgga ggaaggtggg gacgacgtca    1200
aatcatcatg ccccttatga gctgggctac acacgtgcta caatggatgg tacaacgagt    1260
cgcgaaaccg cgaggtcaag ctaatctctt aaagccattc tcagttcgga ttgcaggctg    1320
caactcgcct gcatgaagtt ggaatcacta gtaatcgtgg atcagcatgc cacggtgaat    1380
acgttcccgg gccttgtaca caccgcccgt cacaccatga gagtttgtaa cacccaaaga    1440
cgatggggta accttttagg agctagtcgt ctaaggtggg acagatgatt agggtgaag     1499

<210> SEQ ID NO 2
<211> LENGTH: 1499
<212> TYPE: DNA
<213> ORGANISM: Lactobacillus kunkeei

<400> SEQUENCE: 2
gacgaacgct ggcggcgtgc ctaatacatg caagtcgaac gagctctccc aaattgattt      60
tatgcttgca taaatgattt ttggattcgg agcgagtggc gaactggtga gtaacacgtg     120
ggtaacctgc cccgaagcgg gggataacat ttggaaacaa rtgctaatac cgcataatta     180 gttgaaccg catggttcca acttgaaaga tggctctgct atcactttgg gatggacccg      240
cgccgtatta gttagttggt gagataaaag cccaccaaga cgatgatacg tagccgacct     300
gagagggtaa tcggccacat tgggactgag acacggccca gactcctacg ggaggcagca     360
gtagggaatc ttccacaatg gacgaaagtc tgatggagca acgccgcgtg agtgatgaag     420
gttttcggat cgtaaaactc tgttgttaaa gaagaacaag tgttagagta actgttaaca     480
```

```
ctttgacggt atttaaccag aaagccacgg ctaactacgt gccagcagcc gcggtaatac      540
gtaggtggca agcgttgtcc ggatttattg ggcgtaaagc gagcgcaggc ggttttgtaa      600
gtctgctgtg aaagccctca gctcaactga ggaagtgcag tggaaactac aaaacttgag      660
tacagaagag gaaagtggaa ctccatgtgt agcggtgaaa tgcgtagata tatggaagaa      720
caccagtggc gaaggcggct ttctggtctg ttactgacgc tgaggctcga aagcatgggt      780
agcgaacagg attagatacc ctggtagtcc atgccgtaaa cgatgaatac taggtgttgg      840
agggtttccg cccttcagtg ccgcagctaa cgcattaagt attccgcctg gggagtacga      900
ccgcaaggtt gaaactcaaa ggaattgacg ggggcccgca caagtggtgg agcatgtggt      960
ttaattcgat gctacgcgaa gaaccttacc agctcttgac atcttctgcy aacccaagag     1020
attgggcgtt cccttcgggg acagaatgac aggtggtgca tggttgtcgt cagctcgtgt     1080
cgtgagatgt tgggttaagt cccgcaacga gcgcaaccct tattattagt tgccagcatt     1140
tagttgggca ctctagtgag actgccggtg ataaaccgga ggaaggtggg gacgacgtca     1200
aatcatcatg ccccttatga gctgggctac acacgtgcta caatggatgg tacaacgagt     1260
cgcgaaaccg cgaggtcaag ctaatctctt aaagccattc tcagttcgga ttgcaggctg     1320
caactcgcct gcatgaagtt ggaatcacta gtaatcgtgg atcagcatgc cacggtgaat     1380
acgttcccgg gccttgtaca caccgcccgt cacaccatga gagtttgtaa cacccaaaga     1440
cgatggggta acctttta gg agctagtcgt ctaaggtggg acagatgatt agggtgaag     1499
```

<210> SEQ ID NO 3
<211> LENGTH: 10
<212> TYPE: DNA
<213> ORGANISM: Artificial Sequence
<220> FEATURE:
<223> OTHER INFORMATION: primer

<400> SEQUENCE: 3

```
ccgcagccaa                                                              10
```

LACTIC ACID BACTERIUM HAVING IGA PRODUCTION PROMOTING ACTIVITY, AND USE THEREOF

CROSS-REFERENCE TO RELATED APPLICATIONS

This application is a continuation application of, and claims the benefit of priority to, U.S. patent application Ser. No. 14/369,625, filed on Jun. 27, 2014, now U.S. Pat. No. 9,856,451, which is a National Stage application under 35 U.S.C. § 371 of International Application No. PCT/JP2012/083523, having an International Filing Date of Dec. 25, 2012, which claims the benefit of priority of Japanese Application Serial No. 2011-289314, having a filing date of Dec. 28, 2011. The disclosure of each of the foregoing applications is incorporated herein by reference.

TECHNICAL FIELD

The present invention relates to a lactic acid bacterium belonging to *Lactobacillus kunkeei*, which has a high IgA production inducing activity and is immunologically safe; and a food composition, a pharmaceutical composition, a cosmetic composition, and an immunostimulant, each of which comprises the lactic acid bacterium or treated cells of the lactic acid bacterium.

BACKGROUND ART

Among inflammatory bowel diseases (IBD), ulcerative colitis and Crohn's disease are of unknown cause, and are intractable. Factors associated with inflammatory bowel diseases are abnormalities in the intestinal bacterial flora, secretory IgA production disorder of intestinal epithelial cells, cytokines in the intestinal mucosa, and like factors. The primary lesion of ulcerative colitis is nonspecific chronic inflammation in the large intestine mucosa. Because various autoantibodies are observed therein, ulcerative colitis is considered to have characteristics as an autoimmune disease. On the other hand, Crohn's disease is pathologically characterized by noncaseating granulomatous inflammatory lesions, and dysfunction of monocyte/macrophage cells is considered to be one of the causative factors for the disease. In Japan, the number of ulcerative colitis patients and Crohn's disease patients has steadily increased by slightly less than 10 percent per year, which is problematic.

IBD used to be considered an autoimmune disease. However, with recent advances in research, the inflammation has now been deemed to be caused by intestinal bacteria. It has been reported that intestinal mucosa of IBD patients is less protective against endogenous microflora than in controls, which results in an increase of bacteria in the lumen (see *Gastroenterology*, 1999, 117: 1089-1097). The use of probiotics as a therapy has been the focus of attention since probiotics were reported to have an effect of preventing and alleviating enteritis. There have been many reports on the treatment of IBD with probiotics (Non-patent Literature (NPL) 1).

Lactic acid bacteria, ingested in the form of fermented milk or the like, are known to exhibit various physiological effects based on their functionality, such as regulation of intestinal functions and reduction of serum cholesterol. As physiological effects of lactic acid bacteria, effects on autoimmune diseases such as chronic rheumatoid arthritis and insulin-dependent diabetes, and inflammatory bowel diseases such as irritable bowel syndrome, ulcerative colitis, and Crohn's disease, have begun to receive attention.

Patent Literature (PTL) 1 discloses that cell debris obtained by crushing bacterial cells of one or more species of lactic acid bacteria selected from the group consisting of lactic acid bacteria belonging to the genera *Lactobacillus*, *Lactococcus*, and *Streptococcus*, has interleukin-10 and interleukin-12 production regulating ability, and the application of this product to Crohn's disease and refractory inflammatory bowel diseases is disclosed.

Patent Literature (PTL) 2 discloses that lactic acid bacteria belonging to *Lactobacillus salivarius*, which are highly adhesive to mucous membranes and have high proliferation ability and high resistance to acids, are applicable to prevention and/or treatment of ulcerative colitis and Crohn's disease.

Non-patent Literature (NPL) 2 presents experimental results which show that *Lactobacillus casei* strain GG has the potential to increase the gut IgA immune response and thereby to promote the gut immunological bather, and reports that *Lactobacillus* GG could provide an adjunct nutritional therapy for Crohn's disease.

Non-patent Literature (NPL) 3 reports research results which show that *Lactobacillus* GG may improve gut barrier function and clinical status in children with Crohn's disease.

Non-patent Literature (NPL) 4 reports that intranasal administration of *Lactobacillus rhamnosus* GG protects mice from influenza virus infection by enhancing respiratory cell-mediated immune responses.

There is also a report that IFN-γ and IL-2 mRNA levels in the mucosa of patients with Crohn's disease are significantly increased, compared to controls, and that chronic intestinal inflammation in patients with Crohn's disease is characterized by an increase of Th1-like cytokines (Non-patent Literature (NPL) 5).

Non-patent Literature (NPL) 6 reports that *Lactobacillus kunkeei*, which is a new species belonging to the genus *Lactobacillus*, was isolated from wine. Further, Non-patent Literature (NPL) 7 reports that a fructophilic lactic acid bacteria strain was isolated from a fructose-rich site (flowers), and that the strain was found to contain *Lactobacillus kunkeei*. Patent Literature (PTL) 3 reports that *Lactobacillus kunkeei* was isolated from honeybees.

CITATION LIST

Patent Literature

PLT 1: JP2007-269737A
PLT 2: WO2002/016554
PTL 3: JP2010-525809A

Non-Patent Literature

NPL 1: *Journal of Intestinal Microbiology*, 2009, 23: 193-201
NPL 2: *Annals of Nutrition and Metabolism*, 1996, 40: 137-145
NPL 3: *Journal of Pediatric Gastroenterology and Nutrition*, 2000, 31: 453-457
NPL 4: *Letters in Applied Microbiology*, 2010, 50: 597-602
NPL 5: *Clinical and Experimental Immunology*, 1995, 101: 428-435
NPL 6: *Journal of Applied Microbiology*, 1998, 84: 698-702
NPL 7: *Systematic and Applied Microbiology*, 2009, 32: 593-600

SUMMARY OF INVENTION

Technical Problem

Lactic acid bacteria that have such excellent IgA production inducing activity and that do not induce non-specific cell-mediated immune responses are highly useful, and the development of such lactic acid bacteria has been desired.

Accordingly, an object of the present invention is to provide a lactic acid bacterium belonging to *Lactobacillus kunkeei*, the bacterium having high IgA production inducing activity and being immunologically safe. Another object of the present invention is to provide a food composition, a pharmaceutical composition, a cosmetic composition, and an immunostimulant, each of which comprises the lactic acid bacterium or treated cells of the lactic acid bacterium.

Solution to Problem

The present inventors conducted extensive research to achieve the above objects. As a result, the inventors found that lactic acid bacteria belonging to *Lactobacillus kunkeei*, which were isolated from bee pollen and identified, have a significantly higher IgA production inducing activity than that of *Lactobacillus* strain GG (ATCC534103), and have a significantly lower mitogenic activity and a significantly lower IL-2 production inducing activity than those of *Listeria* strain EGD. The mitogenic activity and IL-2 production inducing activity of the lactic acid bacteria are substantially at the same levels as those achieved without stimulation, and are extremely low, even when compared with heat-killed *Listeria* bacteria. Therefore, these lactic acid bacteria are considered to have no ability to induce non-specific cellular immunity. That is, the lactic acid bacteria are immunologically safe materials.

The present invention was accomplished as a result of further research based on these findings, and provides the following lactic acid bacterium, compositions comprising the lactic acid bacterium, or the like.

(I) Lactic Acid Bacterium (I-1) A lactic acid bacterium belonging to *Lactobacillus kunkeei*, the bacterium having a higher IgA production inducing activity than that of *Lactobacillus* strain GG (ATCC53103), and a lower mitogenic activity and a lower IL-2 production inducing activity than those of *Listeria* strain EGD.

(I-2) The lactic acid bacterium according to item (I-1), which assimilates glucose, fructose, sucrose, trehalose, and gluconate.

(I-3) The lactic acid bacterium according to item (I-1) or (I-2), wherein the source from which the lactic bacterium is isolated is honeybees or apiculture products.

(I-4) The lactic acid bacterium according to any one of items (I-1) to (I-3), which is *Lactobacillus kunkeei* BPS402 (FERM BP-11439) or *Lactobacillus kunkeei* BPS104 (FERM BP-11438).

(II) Composition 1

(II-1) A food composition comprising the lactic acid bacterium according to any one of items (I-1) to (I-4), or treated cells thereof.

(II-2) A pharmaceutical composition comprising the lactic acid bacterium according to any one of items (I-1) to (I-4), or treated cells thereof.

(II-3) A cosmetic composition comprising the lactic acid bacterium according to any one of items (I-1) to (I-4), or treated cells thereof.

(III) Immunostimulant (III-1) An immunostimulant for preventing infection by pathogens or viruses that invade through the respiratory or esophageal mucosa, comprising the lactic acid bacterium according to any one of items (I-1) to (I-4), or treated cells thereof.

(III-2) An intestinal immunostimulant for preventing or alleviating food poisoning, comprising the lactic acid bacterium according to any one of items (I-1) to (I-4), or treated cells thereof.

(IV) Composition 2

(IV-1) A composition for intestinal regulation, beautification, or anti-aging, comprising the lactic acid bacterium according to any one of items (I-1) to (I-4), or treated cells thereof.

(IV-2) A composition for preventing and/or treating an inflammatory bowel disease, comprising the lactic acid bacterium according to any one of items (I-1) to (I-4), or treated cells thereof.

(IV-3) The composition according to items (IV-2), wherein the inflammatory bowel disease is Crohn's disease or ulcerative colitis.

(IV-4) The composition according to any one of (IV-1) to (IV-3), which is a food or a medicament.

Advantageous Effect of the Invention

The lactic acid bacterium belonging to *Lactobacillus kunkeei* according to the present invention has excellent characteristics of having high IgA production inducing activity and being immunologically safe. The lactic acid bacterium is useful in the fields of foods, drugs, cosmetics, etc.

Because the lactic acid bacterium of the present invention has the above characteristics, the following effects are expected: immunostimulation for preventing infection by pathogens or viruses that invade through the respiratory or esophageal mucosa; intestinal immunostimulation for preventing or alleviating food poisoning; intestinal regulation, beautification, or anti-aging; and prevention and/or treatment of an inflammatory bowel disease, such as Crohn's disease or ulcerative colitis.

BRIEF DESCRIPTION OF THE DRAWINGS

In FIG. 6, the relative value of the amount of intrapulmonary virus genome in each sample is presented with standard deviations (**: significant differences at P<0.05).

In FIG. 7, the average of the measurements in each sample is presented with standard deviations (**: significant differences at P<0.05).

DESCRIPTION OF EMBODIMENTS

Figure 1:
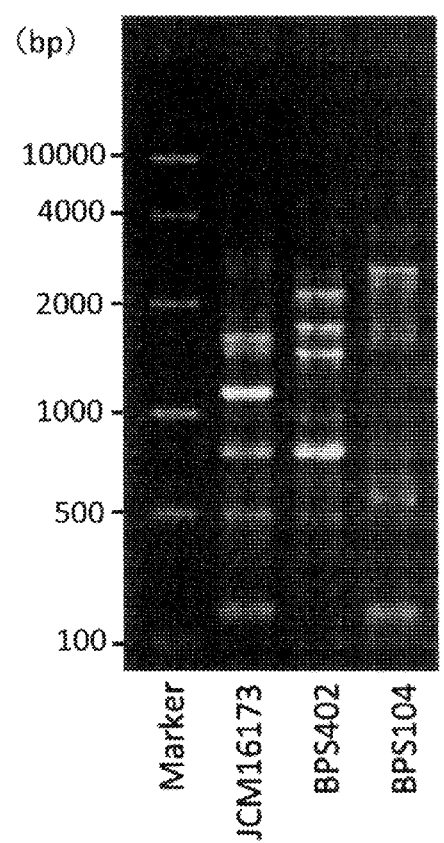
FIG. 1 shows the results of agarose gel electrophoresis of RAPD PCR of *Lactobacillus kunkeei* strains BPS402 and BPS104, and strain JCM 16173, which were electrophoresed on 1% agarose gel at 50V for 1 hour and 30 minutes and stained with EtBr.

The present invention is described in detail below.
Lactic Acid Bacterium

The lactic acid bacterium belonging to *Lactobacillus kunkeei* according to the present invention is characterized by having a higher IgA production inducing activity than that of the *Lactobacillus* strain GG (ATCC534103), and a lower mitogenic activity and a lower IL-2 production inducing activity than those of *Listeria* strain EGD.

The lactic acid bacterium of the present invention is preferably a lactic acid bacterium that assimilates glucose, fructose, sucrose, trehalose, and gluconate. The source from which the lactic acid bacterium of the present invention is isolated is preferably honeybees or apiculture products (honeybee products). In the present invention, an apiculture product refers to a product obtained by breeding honeybees. Examples of such products include honey, royal jelly, propolis, beeswax, bee bread, bee pollen, bee larvae, and processed products thereof (such as extracts). A lactic acid bacterium isolated from bee pollen is particularly preferable as the lactic acid bacterium of the present invention.

There are many reports on excellent IgA production inducing ability provided by oral administration of *Lactobacillus* strain GG (ATCC53103) to patients with Crohn's disease, etc. (*Annals of Nutrition and Metabolism*, 1996, 40: 137-145; *Pediatric Research*, 1992, 32: 141-144; *Journal of Pediatric Gastroenterology and Nutrition*, 1995, 20: 333-338; and *FEMS Immunology and Medical Microbiology*, 2000, 29: 47-52). Accordingly, a material having IgA production inducing activity higher than that of *Lactobacillus* strain GG is considered to have remarkably high IgA production inducing activity.

Further, *Listeria* (*Listeria monocytogenes*) is a gram-positive short *bacillus* that causes listeriosis. Only viable bacteria thereof can induce protective cellular immunity; establishing immunity with heat-killed bacteria is not easy (*Japanese Bacteriology Magazine*, 64(4): 365-376, 2009).

Heat-killed *Listeria* strain EGD also has mitogenic activity and IL-2-inducing ability, although the levels of activity and ability are not as high as in viable bacteria (*Immunology*, 1987, 62: 241-248). However, heat sterilization is actually effective for *Listeria* as well as for many food-poisoning bacteria, and is widely known as a means for preventing food poisoning. Accordingly, a material that has mitogenic activity and IL-2 production inducing activity lower than those of heat-killed *Listeria* strain EGD is considered to be immunologically safe.

Specific examples of the lactic acid bacterium belonging to *Lactobacillus kunkeei* of the present invention include *Lactobacillus kunkeei* strain BPS402 and *Lactobacillus kunkeei* strain BPS104 isolated from bee pollen and identified by the present inventors (hereinafter sometimes simply referred to as "strain BSP402" and "strain BSP104"). These strains were deposited with the National Institute of Advanced Industrial Science and Technology (Independent Administration Corporation), International Patent Organism Depositary (Chuo Dai-6, 1-1 Higashi 1-Chome, Tsukuba-shi, Ibaraki-ken, Japan, (postal code: 305-5466)) under the accession numbers FERM P-22177 and FERM P-22176 on Oct. 3, 2011. These strains were transferred to an international deposit, and have been deposited under the accession numbers FERM BP-11439 and FERM BP-11438.

The following are mycological properties and genetic properties of the strains BPS402 and BPS104.
*Lactobacillus kunkeei* Strain BPS402
Mycological Properties
A. Morphological Characteristics
Cell morphology: *bacillus* (0.7-0.8×1.5-2.0 μm)
Gram stain: positive
Colony color: cream
48 hours of culture on MRS agar plate medium (30° C.)
B. Saccharide Fermentability (Using API 50 CH) Determined after 48 Hours of Culture (Positive: +, Negative: −)

| 0 | Control | − |
|---|---|---|
| 1 | Glycerol | − |
| 2 | Erythritol | − |
| 3 | D-Arabinose | − |
| 4 | L-Arabinose | − |
| 5 | D-Ribose | − |
| 6 | D-Xylose | − |
| 7 | L-Xylose | − |
| 8 | D-Adonitol | − |
| 9 | Methyl-β-D-xylopyranoside | − |
| 10 | D-Galactose | − |
| 11 | D-Glucose | + |
| 12 | D-Fructose | + |
| 13 | D-Mannose | − |
| 14 | L-Sorbose | − |
| 15 | L-Rhamnose | − |
| 16 | Dulcitol | − |
| 17 | Inositol | − |
| 18 | D-mannitol | ? |
| 19 | D-sorbitol | − |
| 20 | Methyl-α-D-mannopyranoside | − |
| 21 | Methyl-α-D-glucopyranoside | − |
| 22 | N-acetylglucosamine | − |
| 23 | Amygdalin | − |
| 24 | Arbutin | − |
| 25 | Esculin ferric citrate | − |
| 26 | Salicin | − |
| 27 | D-Cellobiose | − |
| 28 | D-Maltose | − |
| 29 | D-Lactose | − |
| 30 | D-Melibiose | − |
| 31 | D-Sucrose | + |
| 32 | D-Trehalose | + |
| 33 | Inulin | − |
| 34 | D-Melezitose | − |
| 35 | D-Raffinose | − |
| 36 | Starch | − |
| 37 | Glycogen | − |
| 38 | Xylitol | − |
| 39 | Gentiobiose | − |
| 40 | D-Turanose | − |
| 41 | D-Lyxose | − |
| 42 | D-Tagatose | − |

| | | |
|---|---|---|
| 43 | D-Fucose | − |
| 44 | L-Fucose | − |
| 45 | D-Arabitol | − |
| 46 | L-Arabitol | − |
| 47 | Gluconate | + |
| 48 | 2-Keto-gluconate | − |
| 49 | 5-Keto-gluconate | − |

Genetic Properties

SEQ ID NO: 1 in the sequence list shows the base sequence of 16S rRNA of the strain BPS402. The sequence of 16S rRNA of the strain BPS402 has 100% identity to *Lactobacillus kunkeei* strain YH-15 (JCM16173), which is a reference strain of a known species. The results of simplified molecular phylogenetic analysis showed that the strain BPS402 formed a cluster together with *Lactobacillus kunkeei*, and that both were in the same molecular phylogenetic position. It is determined from these results that the strain BPS402 is a lactic acid bacterium belonging to *Lactobacillus kunkeei*.

*Lactobacillus kunkeei* Strain BPS104
Mycological Properties
A. Morphological Characteristics
Cell morphology: *Bacillus* (0.6-0.7×1.2-1.5 μm)
Gram stain: positive
Colony color: milky-white
72 hours of culture on an MRS agar plate medium (30° C.)
B. Saccharide Fermentability (Using API 50 CH) Determined after 48 Hours of Culture (Positive: +, Negative: −)

| | | |
|---|---|---|
| 0 | Control | − |
| 1 | Glycerol | − |
| 2 | Erythritol | − |
| 3 | D-Arabinose | − |
| 4 | L-Arabinose | − |
| 5 | D-Ribose | − |
| 6 | D-Xylose | − |
| 7 | L-Xylose | − |
| 8 | D-Adonitol | − |
| 9 | Methyl-β-D-xylopyranoside | − |
| 10 | D-Galactose | − |
| 11 | D-Glucose | + |
| 12 | D-Fructose | + |
| 13 | D-Mannose | − |
| 14 | L-Sorbose | − |
| 15 | L-Rhamnose | − |
| 16 | Dulcitol | − |
| 17 | Inositol | − |
| 18 | D-Mannitol | ? |
| 19 | D-Sorbitol | − |
| 20 | Methyl-α-D-mannopyranoside | − |
| 21 | Methyl-α-D-glucopyranoside | − |
| 22 | N-Acetylglucosamine | − |
| 23 | Amygdalin | − |
| 24 | Arbutin | − |
| 25 | Esculin Ferric Citrate | − |
| 26 | Salicin | − |
| 27 | D-Cellobiose | − |
| 28 | D-Maltose | − |
| 29 | D-Lactose | − |
| 30 | D-Melibiose | − |
| 31 | D-Sucrose | + |
| 32 | D-Trehalose | + |
| 33 | Inulin | − |
| 34 | D-Melezitose | − |
| 35 | D-Raffinose | − |
| 36 | Starch | − |
| 37 | Glycogen | − |
| 38 | Xylitol | − |
| 39 | Gentiobiose | − |
| 40 | D-Turanose | − |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Gluconate | + |
| 48 | 2-Keto-gluconate | − |
| 49 | 5-Keto-gluconate | − |

Genetic Properties

SEQ ID NO: 2 in the sequence list shows the base sequence of 16S rRNA of the strain BPS402. The sequence of 16S rRNA of the strain BPS104 has 99.9% identity to *Lactobacillus kunkeei* strain YH-15 (JCM16173), which is a reference strain of a known species. The results of simplified molecular phylogenetic analysis showed that the strain BPS104 formed a cluster together with *Lactobacillus kunkeei*, and that both were in the same molecular phylogenetic position. It is determined from these results that the strain BPS104 is a lactic acid bacterium belonging to *Lactobacillus kunkeei*.

Table 1 below shows the summary of test results of saccharide fermentability of the strain BPS402, strain BPS104, and *Lactobacillus kunkeei* (JCM16173). Table 1 shows that the saccharide fermentability of the strain BPS402 and strain BPS104 is different from that of the known strain.

TABLE 1

| | Glucose | Fructose | Sucrose | Trehalose | Gluconate |
|---|---|---|---|---|---|
| *L. kunkeei* (JCM16173) | + | − | + | − | − |
| BPS402 | + | + | + | + | + |
| BPS104 | + | + | + | + | + |

Results of determination after 48 hours
Positive: +,
Negative: −

Random amplified polymorphic DNA (RAPD) analysis was performed using a primer 5'-CCGCAGCCAA-3' under the following reaction conditions. Preincubation: 94° C. for 2 minutes, amplification: 94° C. for 1 minute, 30° C. for 1 minute, and 72° C. for 1.5 minutes (40 cycles), and primer extension: 74° C. for 5 minutes (1 cycle).

FIG. 1 shows the results. The results of FIG. 1 show that the RAPD patterns of the strains BPS402 and BPS104 are different from those of known *Lactobacillus kunkeei* strains.

It was determined from these results that the strains BPS402 and BPS104 are novel *Lactobacillus kunkeei* strains.

These strains can be cultured in a usual manner. There is no specific limitation on the medium to be used, as long as these strains can be cultured therein. Natural media, synthetic media, semisynthetic media, and like media can be used. Milk, royal jelly, etc., can also be used as media. As the medium, media containing a nitrogen source and a carbon source can be used. Examples of nitrogen sources include meat extract, peptone, casein, yeast extract, gluten, soybean flour, soybean hydrolyzate, amino acids, and the like. Examples of carbon sources include glucose, lactose, fructose, inositol, sorbitol, starch syrup, starch, rice malt extract, wheat bran, bagasse, molasses, and the like. Further, minerals (such as ammonium sulfate, potassium phosphate, magnesium chloride, sodium chloride, calcium carbonate, iron, manganese, and molybdenum), various vitamins, etc. can be added.

The culturing temperature is typically 4 to 45° C., and preferably 30 to 37° C. The culturing time is typically about 8 to 72 hours. Aeration-shaking or aeration-agitation may be performed. The pH of the medium is typically 4.0 to 9.0, and preferably 6.0 to 8.0.

An example of the culture method is a method comprising inoculating the cells at a concentration of 1% into MRS medium, and culturing the cells at 37° C. for 24 hours.

Food Composition

The food composition of the present invention comprises the lactic acid bacterium or treated cells of the lactic acid bacterium as an essential component. The food composition includes all food compositions that can be ingested by animals (including humans).

The food composition of the present invention contains the lactic acid bacterium that may be either viable or heat-killed. As the lactic acid bacterium, isolated cells may be used, or a cell culture or fermentation product thereof may be used.

Examples of the treated cells of the lactic acid bacterium include those obtained by subjecting the lactic acid bacterium to heating, pasting, drying (freeze-king, vacuum-drying, spray-king, etc.), freezing, lysis, crushing, extraction, etc. Examples of the treated cells further include supernatants obtained by removing proteins from cell debris obtained by sonication or other disintegration techniques, supernatants obtained by removing the solids from a cell culture or fermentation product thereof, etc.

The lactic acid bacterium may be used alone, or in admixture with other microorganisms.

To prepare the food composition of the present invention, the lactic acid bacterium or treated cells thereof may be used without further processing, or, if necessary, may be mixed with minerals, vitamins, flavonoids, quinones, polyphenols, amino acids, nucleic acids, essential fatty acids, fresheners, binders, sweeteners, disintegrators, lubricants, coloring agents, fragrances, stabilizing agents, preservatives, sustained-release regulators, surfactants, solubilizers, wetting agents, and the like.

The type of food composition according to the present invention is not particularly limited, and examples thereof include dairy products; fermented foods (yogurt, royal jelly, etc.); beverages (coffee, juices, tea drinks, and like soft drinks, milk beverages, lactic acid bacteria beverages, drinks containing lactic acid bacteria, yogurt drinks, carbonated drinks, Japanese sake, Western wines and spirits, fruit wines, and like liquors, etc.); spreads (custard cream, etc.); pastes (fruit pastes, etc.); Western-style confectioneries (chocolate, doughnut, pie, cream puff, gum, jelly, candies, cookies, cakes, pudding, etc.); Japanese sweets (daifuku [rice cake stuffed with sweet beans], rice cake, manju [steamed yeast bun with filling], kasutera [Castella sponge cakes], anmitsu [gelatin mixed with other ingredients], yokan [azuki bean jelly], etc.); frozen desserts (ice creams, ice candies, sherbets, etc.); foods (curry, gyudon [beef and onion stew on top of a bowl of rice], zousui [risotto], miso soup, soup, meat sauce, pasta, pickles, jam, royal jelly, etc.); seasonings (dressing, furikake [a mixture of dried fish and/or vegetable flakes for sprinkling on steamed rice], tasty seasonings, soup bases, etc.); etc.

The method for producing the food composition of the present invention is also not particularly limited, and can be suitably performed according to a known method. For example, the lactic acid bacterium or treated cells thereof may be mixed into or sprayed over the intermediate or final product obtained in a process of producing such a food composition as described above, thereby obtaining a food. Fermented products, lactic acid bacteria beverages, and drinks containing lactic acid bacteria can be obtained by fermenting cow's milk or like animal milks, milk raw materials, etc., with the lactic acid bacterium. The fermented foods of royal jelly can also be produced by fermenting royal jelly with the lactic acid bacterium.

The food composition of the present invention can also be used as health foods, functional foods, nutraceuticals, dietary supplements, foods for health uses, foods for specified health uses, or probiotic products. The dosage unit form of the composition for use as a dietary supplement is not particularly limited, and can be suitably selected. Examples of such dosage forms include tablets, capsules, granules, liquids, powders, and the like.

The content of the lactic acid bacterium or treated cells thereof in the food composition of the present invention can be suitably selected from $1 \times 10^{-7}$ to 100 wt. %, preferably $1 \times 10^{-5}$ to 100 wt. %, and more preferably 1 to 100 wt. %.

The amount of intake of the food composition of the present invention can be suitably set according to various conditions, such as the consumer's body weight, age, sex, and symptoms. The daily intake expressed by the number of lactic acid bacterium may be, for example, $1 \times 10^6$ or more, preferably $1 \times 10^9$ or more, and more preferably $1 \times 10^{12}$ or more.

Pharmaceutical Composition

The pharmaceutical composition of the present invention comprises the lactic acid bacterium or treated cells thereof as an essential ingredient. The pharmaceutical composition of the present invention can be referred to as a lactic acid bacteria preparation.

The pharmaceutical composition of the present invention contains the lactic acid bacterium that may be either viable or heat-killed. As the lactic acid bacterium, isolated cells may be used, or a cell culture or fermentation product thereof may be used.

Examples of the treated cells of the lactic acid bacterium include those obtained by subjecting the lactic acid bacterium to heating, pasting, drying (freeze-drying, vacuum-drying, spray-drying, etc.), freezing, lysis, etc. Examples of the treated cells further include supernatants obtained by removing proteins from cell debris obtained by sonication or other disintegration techniques, supernatants obtained by removing the solids from a cell culture or fermentation product thereof, etc.

The lactic acid bacterium may be used alone, or in admixture with other microorganisms.

To prepare the pharmaceutical composition, the lactic acid bacterium or treated cells thereof may be used without further processing, or mixed with a pharmaceutically acceptable non-toxic carrier, diluent, or excipient, and formed into tablets (including uncoated tablets, sugar-coated tablets, effervescent tablets, film-coated tablets, chewable tablets, troches, etc.), capsules, pills, powder (powdered drugs), fine granules, granules, liquids, suspensions, emulsions, syrups, pastes, and injections (including preparations formulated into liquids by admixture into distilled water or an infusion, such as an amino acid infusion or an electrolyte infusion, before use).

The content of the lactic acid bacterium or treated cells thereof in the pharmaceutical composition of the present invention can be suitably selected from $1 \times 10^{-7}$ to 100 wt. %, preferably $1 \times 10^{-5}$ to 100 wt. %, and more preferably 1 to 100 wt. %.

The dose of the pharmaceutical composition of the present invention can be suitably set according to various conditions, such as the patient's body weight, age, sex, and symptoms. The daily dose expressed by the number of lactic acid bacterium may be, for example, $1\times10^{10}$ or more, preferably $1\times10^{11}$ or more, and more preferably $1\times10^{12}$ or more.

The lactic acid bacterium or treated cells thereof according to the present invention can also be used as an immunostimulant for preventing infection by a pathogen or a virus that invades through the respiratory or esophageal mucosa, or as an intestinal immunostimulant for preventing or alleviating food poisoning. Examples of the virus that the respiratory or esophageal mucosa include, but are not limited to, influenza viruses.

The food or pharmaceutical composition of the present invention is effective for intestinal regulation, beautification, or anti-aging, and preventing and/or treating inflammatory bowel diseases (preferably Crohn's disease or ulcerative colitis).

Cosmetic Composition

The cosmetic composition of the present invention contains the lactic acid bacterium or treated cells thereof as an essential component.

The cosmetic composition of the present invention contains the lactic acid bacterium that may be either viable or heat-killed. As the lactic acid bacterium, isolated cells may be used, or a cell culture or fermentation product thereof may be used.

Examples of the treated cells of the lactic acid bacterium include those obtained by subjecting the lactic acid bacterium to heating, pasting, drying (freeze-drying, vacuum-drying, spray-drying, etc.), freezing, lysis, etc. Examples of the treated cells further include supernatants obtained by removing proteins from cell debris obtained by sonication or other disintegration techniques, supernatants obtained by removing the solids from a cell culture or fermentation product thereof, etc.

The lactic acid bacterium may be used alone, or in admixture with other microorganisms.

The cosmetic composition of the present invention includes all cosmetic compositions that are applied to the skin, mucosa, body hair, head hair, scalp, nails, teeth, facial skin, lips, etc. of animals (including humans).

The content of the lactic acid bacterium or treated cells thereof in the cosmetic composition of the present invention can be suitably selected from the range of $1\times10^{-10}$ to 100 wt. %, preferably $1\times10^{-6}$ to 50 wt. %, and more preferably $1\times10^{-2}$ to 10 wt. %.

The cosmetic composition of the present invention may contain, in addition to the lactic acid bacterium or treated cells thereof, ingredients commonly used in cosmetics, such as skin-lightening agents, moisturizers, antioxidants, oily components, ultraviolet absorbers, surfactants, thickeners, alcohols, powder constituents, color materials, aqueous ingredients, water, various skin nutrients, etc.

The cosmetic composition of the present invention can be formulated into a wide range of dosage forms, such as aqueous solutions, solubilizers, emulsions, powders, oils, gels, ointments, aerosols, water-oil bilayer preparations, and water-oil-powder trilayer preparations.

The cosmetic composition of the present invention may be used for any purpose of use. Examples of such uses include basic cosmetics such as facial washes, face lotions, milky lotions, creams, gels, essences, beauty essences, packs, and masks; make-up products such as foundations, lipsticks, blushes, eye shadows, eyeliners, and mascaras; nail cosmetics such as nail polishes, base coats, topcoats, and nail polish removers; and other products such as facial washes, massaging agents, cleansing agents, after-shave lotions, pre-shave lotions, shaving creams, body soaps, soaps, shampoos, rinses, hair treatments, hair dressings, hair tonics, hair growing agents, antiperspirants, and bath agents.

The cosmetic composition of the present invention is expected to exhibit anti-aging effects, such as skin-lightening effects and moisturizing effects.

EXAMPLES

The present invention is described below in more detail with reference to Examples. However, the present invention is not limited thereto or thereby.

Screening of *Lactobacillus kunkeei* Strains BPS402 and BPS104

The medium used for isolating the bacteria was an MRS culture medium (or ROGOSA medium). Any of apple juice, orange juice, tomato juice, or grape juice was added as desired to achieve a final concentration of 25%, and the medium was adjusted to pH 4.5 with acetic acid and sodium hydroxide. Bee pollen was appropriately diluted in the prepared medium, and culture was started at 25 to 37° C. in an incubator. After 2 to 3 days of culture, the cells were spread on MRS agar medium containing calcium carbonate by a streak method, and culture was further continued at the same temperature as above for another two to three days to obtain single colonies having a clear zone by lactic acid production. The obtained colonies were cultured in MRS, and then cryopreserved at −80° C. as a 10% glycerol stock.

In particular, the amount of IgA production (O.D.≥0.2), and mitogenic activity and IL-2 production (S.I. value≤1.2) were used as screening indices in the present test examples. For mitogenic activity and IL-2 production, S.I. value without stimulation was set as 1.0.

TEST EXAMPLES

Test Example 1

Experimental Method
Breeding/Feeding of Animals

Six-week-old female BALB/c mice preliminarily bred for one week after completion of quarantine and inspection were used. The individuals that had similar body weights and exhibited similar changes in body weight during the preliminary breeding were selected as test animals.

Preparation of Cells

In accordance with the test animal breeding and feeding laws, the blood was collected from the animals under anesthesia to exsanguinate the animals. After the exsanguination, spleen and small intestine (including cecum and ileocecum) were excised, and transferred to Petri dishes containing a 1% BSA-containing Hank's solution, and stored ice-cold. Spleen-derived lymphocytes (SPL) were collected from the spleen, and Peyer's patch-derived lymphocytes (PPL) were collected from the small intestine. Cells of each type were resuspended in 10% RPMI-1640 medium to a density of $1\times10^6$ cells/ml.

Preparation of Bacteria

Figure 2:
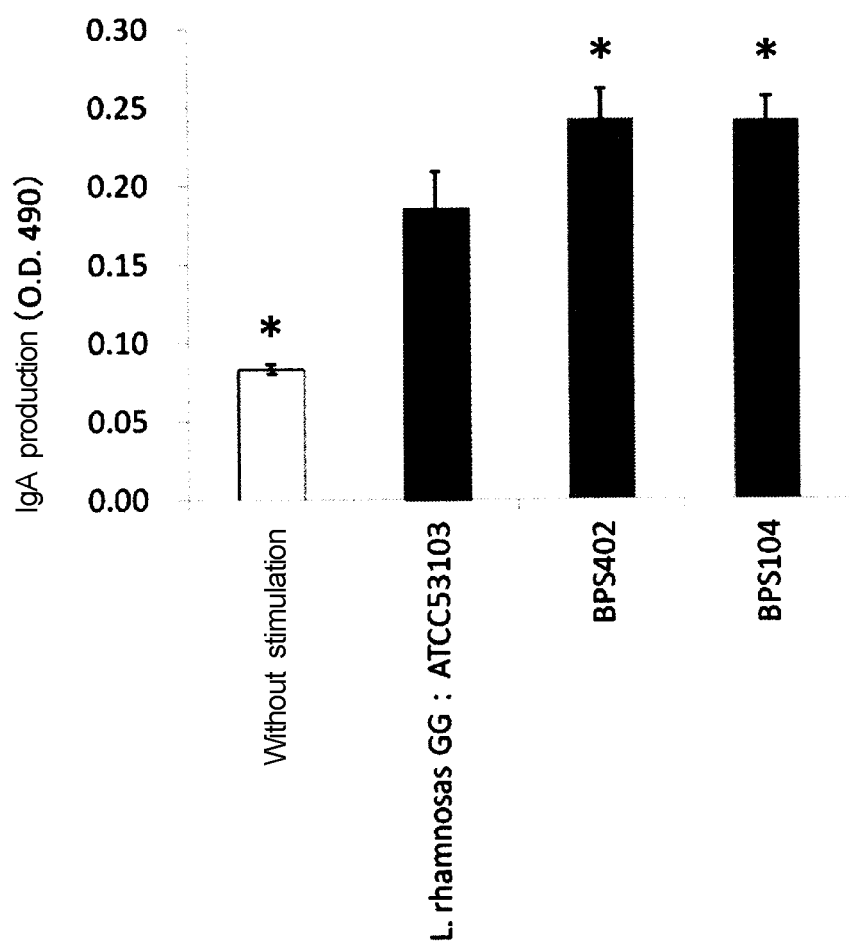
FIG. 2 is a graph showing the IgA production inducing ability of *Lactobacillus kunkeei* strains BPS402 and BPS104. *:p<0.05 (vs. *L. rhamnosus* GG: ATCC53103, Dunnett's Multiple Comparison Test).

Each bacterial strain was streaked on Mueller-Hinton agar medium, and cultured in a 37° C. incubator for 16 hours. Single colonies grown on the agar medium were picked up with a platinum needle, streaked on new Mueller-Hinton agar medium, and cultured in a 37° C. incubator for 16 hours. The cell colonies were lysed in TS liquid medium to a McFarland turbidity (MCF) of 3.0 as a rule of thumb, thus preparing bacterial suspensions. The number of cells in a portion of each bacterial suspension was counted by the tenfold serial dilution method. The obtained bacterial suspensions were heated at 100° C. for 30 minutes, and used as the test substances described in the next section. As a control bacterial strain, *Listeria monocytogenes* (EGD strain) was used, and the same procedure as the above streak culture was performed to an MCF of 3.0 as a rule of thumb to prepare a bacterial suspension. Further, the obtained bacterial suspension was heated at 100° C. for 30 minutes, and used as the control strain described in the next section IgA production inducing ability measurement test The collected PPL was stimulated with one of the test substances as an antigen. Forty-eight hours after the stimulation, the culture supernatant was collected. IgA in the collected culture supernatant was measured by ELISA assay.
Lymphocyte Blastogenesis Test The collected SPL was stimulated with mitogen (PWM final concentration: 5 μg/mL) or with one of the test substances as an antigen in the presence of BrdU-Thymidine. The amount of uptake of BrdU-Thymidine was measured. Further, the culture supernatant was collected using the same system, and a cell proliferation ability test using CTLL-2 cells was conducted.
Results and Discussion
IgA Antibody Production Inducing Ability Peyer's patch cells were stimulated with one of the test substances. The culture supernatant after 48 hours of stimulation was added to an ELISA plate for measuring IgA antibody, and IgA antibody production inducing ability was evaluated. Peyer's patch cells without stimulation were used as a negative control, and the O.D. value obtained using each test substance was evaluated relative to the O.D. value of the negative control. FIG. 2 shows the results.

Figure 3:
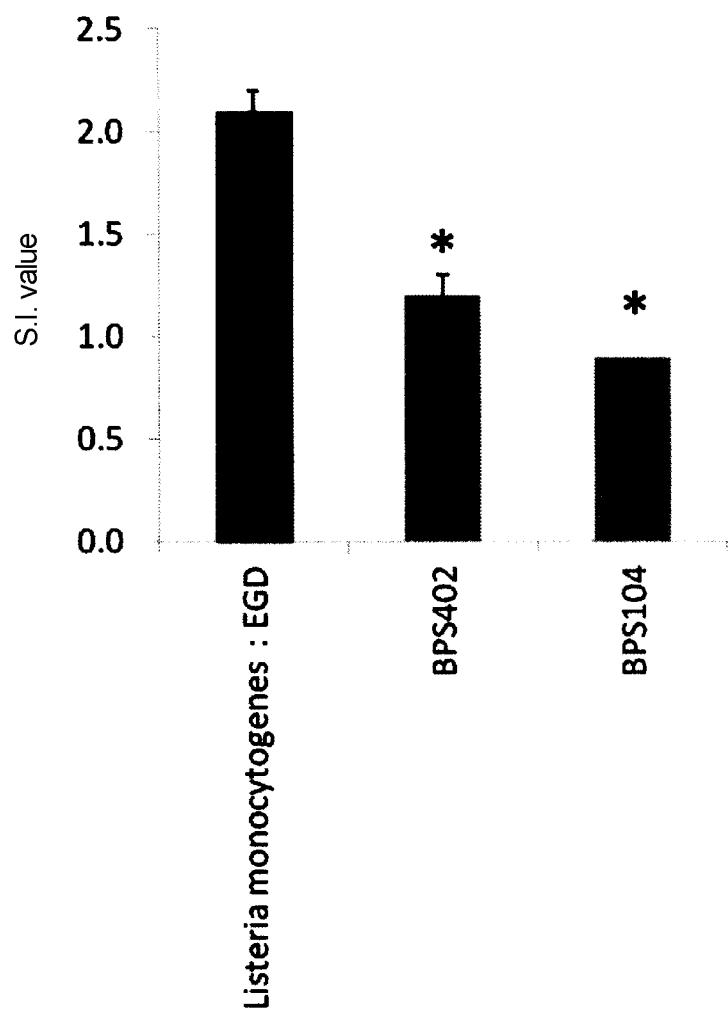
FIG. 3 is a graph showing mitogenic activity (S.I. value) of *Lactobacillus kunkeei* strains BPS402 and BPS104. *: p<0.01 (vs. *Listeria monocytogenes*: EGD, Dunnett's Multiple Comparison Test), S.I. value: stimulation index, the amount of BrdU-Thymidine uptake by spleen-derived lymphocytes (expressed with the uptake amount without stimulation being set as 1.0).

The O.D. values of the strains BPS402 and BPS104 were 0.243 and 0.242, respectively, and the O.D. value obtained using the control strain *Listeria monocytogenes* was 0.107.
Lymphocyte Blastogenesis Response
Spleen Cell Proliferation Responses Determined Using BrdU Uptake as an Indicator Spleen cells were stimulated using one of the test substances. The uptake of fluorescently labeled BrdU-Thymidine was evaluated by fluorescence intensity using a flow cytometer. Spleen cells without stimulation were used as a negative control. The fluorescence intensity obtained using each test substance was evaluated relative to the fluorescence intensity of the negative control. FIG. 3 shows the results.

Figure 4:
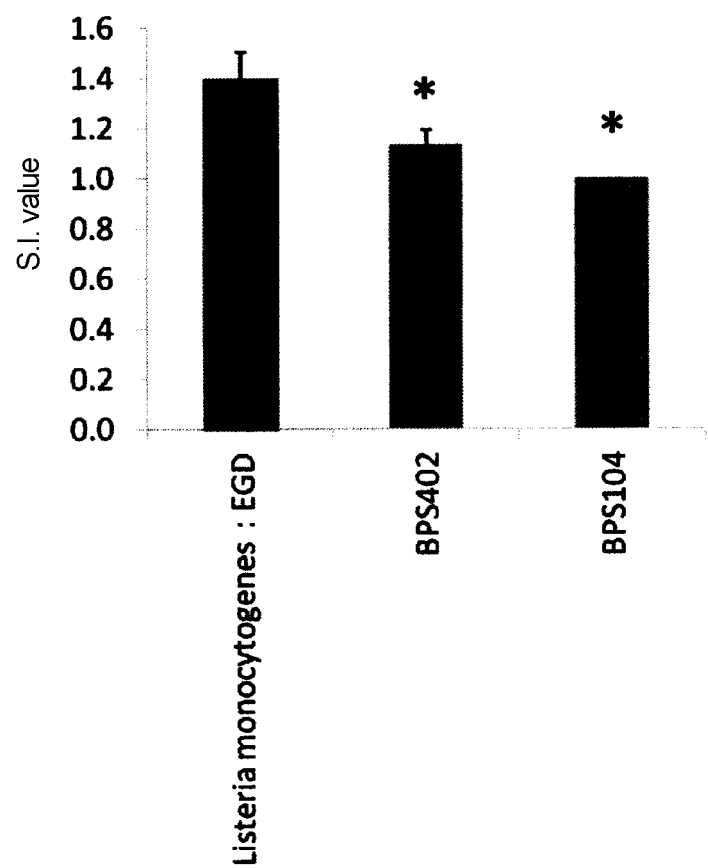
FIG. 4 is a graph showing IL-2 production inducing ability (S.I. value) of *Lactobacillus kunkeei* strains BPS402 and BPS104. *: p<0.01 (vs. *Listeria monocytogenes*: EGD, Dunnett's Multiple Comparison Test), S.I. value: stimulation index, the amount of BrdU-Thymidine uptake by CTLL-2 cells (expressed with the uptake amount without stimulation being set as 1.0).

The S.I. value of the blastogenic response obtained using the control strain *Listeria monocytogenes* was 2.1, whereas S.I. values of the strains BPS402 and BSP104 were 1.2 and 0.9, respectively.
Evaluation of Test Substances Using CTLL-2 Cell Proliferation Response as an Indicator IL-2 in the culture supernatant obtained in the above test was measured using CTLL-2 cells as an indicator. For the measurement, BrdU-Thymidine uptake of CTLL-2 cells was evaluated by fluorescence intensity determined using a flow cytometer. Spleen cells without stimulation were used as a negative control. The fluorescence intensity of each test substance was evaluated relative to the fluorescence intensity of the negative control. FIG. 4 shows the results.

The S.I. value of the blastogenic response obtained using the control strain *Listeria monocytogenes* was 1.4, while the S.I. values of the strains BPS402 and BSP104 were 1.1 and 1.0, respectively.

The heat-killed lactic acid bacterial strains BPS402 and BPS104 did not exhibit such potent mitogenic activity as to induce T cell immune response. Even compared to heat-killed *Listeria* bacteria, which are intracellular parasitic bacteria, the heat-killed lactic acid bacterial strains BPS402 and BPS104 are extremely low in terms of cellular proliferation response and IL-2 production inducing ability, and thus do not have the ability to non-specifically induce cellular immunity. That is, the strains BPS402 and BPS104 do not always enhance immune activity in a host, and are considered to be immunologically safe substances.

It was suggested that the heat-killed lactic acid bacteria may induce IgA production of Peyer's patch cells. Accordingly, the heat-killed lactic acid bacteria are likely to increase the amount of IgA antibody present in mucosal epithelium, such as respiratory mucosa and esophageal mucosa, and is thus considered to be effective for preventing infection of pathogens (such as viruses) that invade through the mouth and nose.

Test Example 2

Test Method
1. Preparation of Virus

MDCK cells cultured in a cell growth medium were infected with an influenza virus (IFVA, strain PR/8/34 (H1N1)), which had been cryopreserved in a deep freezer, at a multiplicity of infection (M.O.I.) of 0.01 and cultured at 37° C. in the presence of 5% $CO_2$ for 72 hours (one passage). Cells serially passaged for 5 passages were mass-produced, and subjected to sucrose gradient centrifugation to separate and purify a viral fluid. The viral fluid was stored in a deep freezer until use. A portion of the virus fluid was subjected to tenfold serial dilution to confirm cytopathic effects, thereby determining the viral infectivity titer ($TCID_{50}$) and plaque-forming unit (pfu).
2. Viability Analysis
a. Oral Administration of Test Substance Six-week-old male BALB/c mice preliminarily bred for one week after completion of the quarantine and inspection were used. Each mouse was given one of the test substances in an amount of 0.2 mL by a single oral gavage. The concentration of each test substance was set to 1 mg per kg of the body weight. A test substance was given by oral gavage once a day throughout the test period, and this administration was continued until the end of the test period after IFVA infection. Physiological saline was orally administered to a negative control group in the same manner as each test substance.
b. Grouping The mice were divided into two test groups. The table below shows the details. The two groups were intranasally inoculated with the prepared IFVA, and 20 mice reliably inoculated with the virus were assigned to each group. For grouping, each mouse was numbered and assigned by stratified randomization when the test substance began to be administered.

TABLE 2

| Test group | Viral infection | Test substance concentration | Number of mice |
|---|---|---|---|
| 1 | + (Intranasal inoculation) | — | 20 |
| 2 | + | 1 mg/kg | 20 | c. IFVA Inoculation

Nine-week-old female BALB/c mice given the test substance by oral gavage for 3 consecutive weeks were used. The mice were intraperitoneally injected with Pentobarbital sodium (5.0 mg/mL; Kyoritsuseiyaku Corporation (trade name; Somnopentyl anesthetic injection) diluted with physiological saline at 50 mg/kg in the order of animal numbering to undergo general anesthesia Under general anesthesia, the prepared IFVA was intranasally inoculated at 103 pfu/20 μL into the right nasal cavity of each mouse.

d. Determination of the Survival Rate

To determine the survival rate, follow-up observations were performed for 3 weeks after IFVA inoculation. The survival rate was determined by dividing the number of individuals that survived during the follow-up observation period by the total number of individuals in each group, and multiplying the obtained value by 100.

3. Immunological Analysis a. Oral Administration of Test Substance

Six-week-old male BALB/c mice preliminarily bred for one week after completion of the quarantine and inspection were used. Each mouse was given the test substance in an amount of 0.2 mL by a single oral gavage. The concentration of the test substance was set to 100 mg per kg of the body weight. The test substance was given by oral gavage once a day throughout the test period, and this administration was continued until the end of the test period after IFVA infection. Physiological saline was orally administered to a negative control group in the same manner as each test substance.

b. Grouping

The mice were divided into a total of four groups: two virus-inoculated groups, and two non-virus-inoculated groups. The table below shows the details. The two virus-inoculated groups were intranasally inoculated with the prepared IFVA, and 50 mice reliably inoculated with the virus were assigned to each group. The number of mice in each of the non-virus-inoculated groups was 10. For grouping, each mouse was numbered and assigned by stratified randomization when the test substance began to be administered.

TABLE 3

| Test group | Viral infection | Test substance concentration | Number of mice | Notes |
|---|---|---|---|---|
| 1 | – (none) | – (Physiological saline) | 10 | For analysis of non-infection (d 0) |
| 2 | – | 100 mg/kg | 10 | For analysis of non-infection (d 0) |
| 3 | + (Intranasal inoculation) | – | 50 | |
| 4 | + | 100 mg/kg | 50 | | c. IFVA Inoculation

Nine-week-old female BALB/c mice given the test substance by oral gavage for 3 consecutive weeks were used. Pentobarbital sodium (5.0 mg/mL; Kyoritsuseiyaku Corporation (trade name; Somnopentyl anesthetic injection) diluted with physiological saline was intraperitoneally injected to the mice at 50 mg/kg in the order of animal numbering to undergo general anesthesia Under general anesthesia, the prepared IFVA was intranasally inoculated at 102 pfu/20 μL into the right nasal cavity of each mouse. 20 μL of physiological saline was intranasally administered to the non-virus-inoculated groups in a similar manner.

d. Collection of Tissue Samples 0 day (d0) and 14 days (d14) after the IFVA infection, eight mice in each group were killed. Bronchioalveolar lavage fluid (BALF) was collected from five mice in each group, while untreated lungs were excised from three mice in each group and preserved in 10% (v/v) formalin.

e. Measurement of the Amount of Pulmonary Viral Genomic RNA

The lungs after the treatment were excised from 5 mice in each group, and cell suspensions were created using a gentle MACS Dissociator (Miltenyi Biotec). Lung-derived total RNA was extracted from each of the cell suspensions using ISOGEN II. The extracted RNA was subjected to a reverse transcription reaction using Uni12 primer (Hoffmann E. et al., Arch Virol., 2001). After selectively amplifying viral genomic RNA, the amount of viral genomic RNA in the lungs was measured by real-time PCR using primers specific to the viral NP gene.

f. Antibody Measurement

The collected BALF was centrifuged and separated into a supernatant and cellular components. The supernatant was stored in a deep freezer until analysis was conducted. The antibody in the BALF supernatant was measured by ELISA. The measurement parameter was anti-influenza virus-specific IgA.

4. Statistical Processing

A comparison in the survival rate analysis between the groups was made using a log-rank test at a two-sided significance level of 0.05. Significance of difference between the groups in other tests was assessed using a Student's t-test at a two-sided significance level of 0.05.

Results and Discussion

Figure 5:
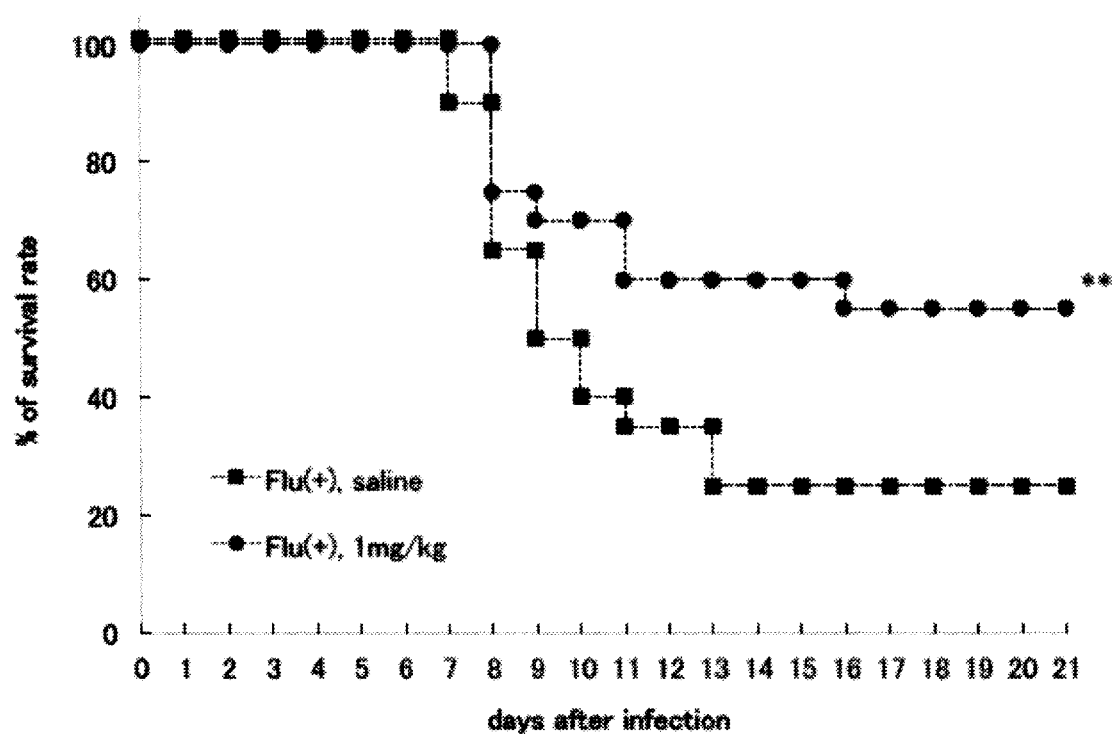
FIG. 5 is a graph showing a comparison of changes in the survival rate of BALB/c mice after infection with an influenza virus (A/PR/8/34 strain) (a physiological saline-administered group vs. a 1 mg/kg-administered group) (**: significant differences at P<0.05 in comparison with the physiological saline-administered group).

1. Survival Rate Analysis (FIG. 5)

The physiological saline-administered group, which is an experimental control group, had a survival rate of 25.0% at the completion of the test. The group given a test substance (lactic acid bacteria BPS402 powder; hereinafter referred to as BPS402) in an amount of 1 mg/kg had a survival rate of 55.0% at the completion of the test. A comparison of the group given BPS402 in an amount of 1 mg/kg to the experimental control group using a log-rank test (p=0.0465) indicated a significant difference.

Figure 6:
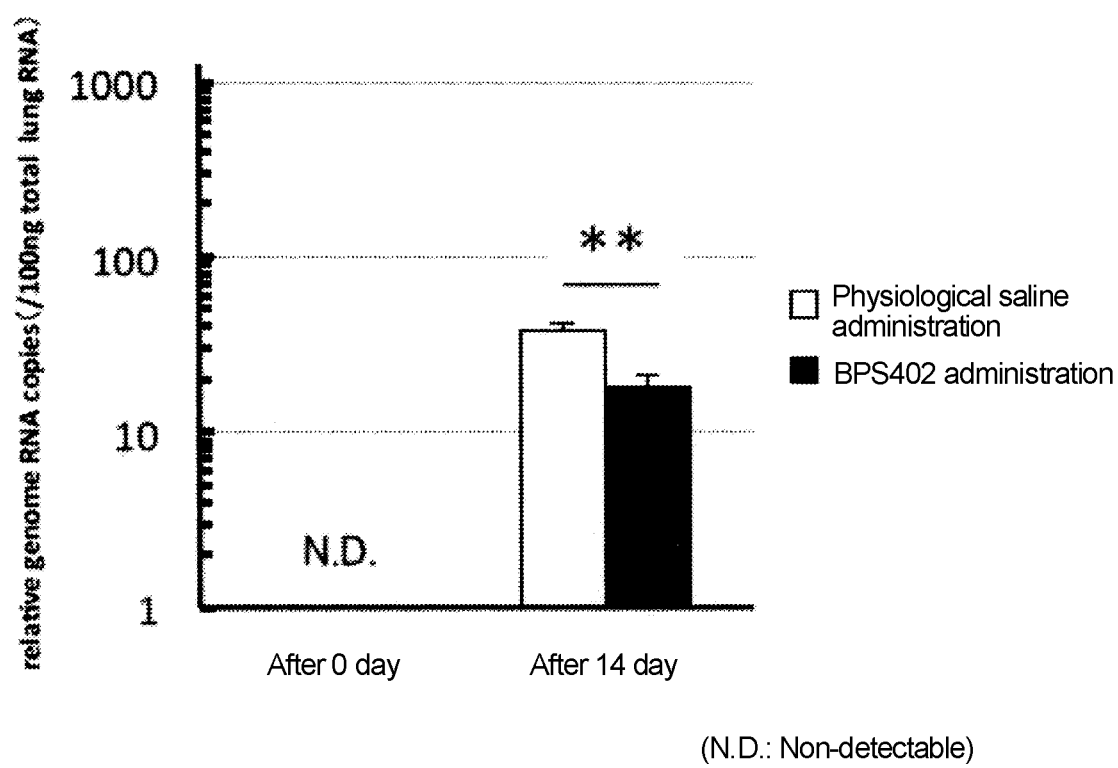
FIG. 6 is a graph showing a comparison of intrapulmonary viral genome amounts in physiological saline-administered mice and BPS402-administered mice after infection with an influenza virus.

The results show that the BPS402-administered group tends to have higher resistance to IFVA infection than the experimental control group. Non-patent Literature (NPL) 4 (Letters in Applied Microbiology, 2010, 50: 597-602) discloses that administration of LGG in an amount of 200 μg/mouse provides an influenza virus-preventing effect, whereas the use of BPS402 in an amount of 20 μg/mouse (the body weight of the mouse is assumed to be 20 g) provided the preventing effect. This indicates that BPS402 was effective at one-tenth the dose of the LGG 2. Immunological Analysis a. Measurement of the Amount of Pulmonary Viral Genomic RNA (FIG. 6)

Figure 7:
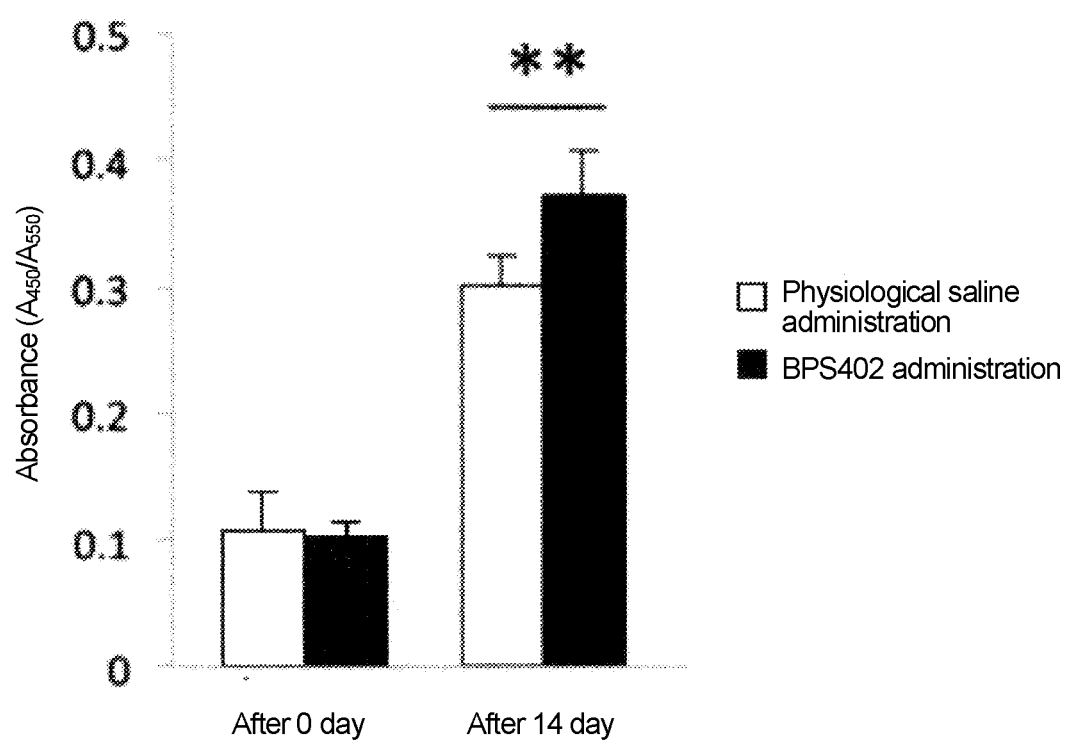
FIG. 7 is a graph showing a comparison of virus-specific IgA in bronchoalveolar lavage fluid (BALF) between physiological saline-administered mice and BPS402-administered mice after infection with an influenza virus.

A signification reduction in viral load in the BPS402-administered group 14 days after the infection was observed.

b. Antibody Measurement (FIG. 7)

A significant increase in the amount of influenza virus-specific IgA was observed in the BALF of IFVA-infected, BPS402-administered mice 14 days after the infection.

As a result of in vivo immunological analysis using the BPS402-administered mice, an elevation of influenza virus-specific secretory IgA in the lung alveoli and bronchi at the late infection stage, and enhanced antiviral effects at the late infection stage were observed in the BPS402-administered group. The results suggest that BPS402 may play a role in quickly overcoming the infection by exerting a particularly strong effect on B-cell lineage plasma cells, and causing efficient secretion of influenza virus-specific IgA.

Test Example 3

The efficacy and safety of *Lactobacillus kunkeei* BPS402 in humans were confirmed in this test.

General paid volunteers who were healthy but tended to be constipated were subjected to a double-blind, placebo-controlled trial. The subjects were paid volunteers aged 40 or older. These subjects were divided into two groups, seven subjects in a BPS402 group and seven subjects in a placebo group, in such a manner that they were as equal as possible in each item. The amount of intake was 5 doses (1,000 mg) per day, and the intake period was four weeks.

Efficacy

A significant elevation of sIgA (μg/min) in saliva was observed after intake of BPS402, compared to that before intake of BPS402. sIgA is widely known as an immunoglobulin having important immunological function in the mucosal system, and is considered to reduce the risk of infection with upper respiratory tract infections.

The degree of dryness of the skin was shown on a linear scale of 0 to 100 mm and analyzed by visual analog scale (VAS). Dryness of the skin was significantly improved after intake of BPS402, compared to that before intake of BPS402, and a moisturizing effect was confirmed.

Safety

Intake of BPS402 created no particular problem in safety.

Production Examples

Production Examples of the compositions of the present invention are shown below.

Production Example of Lactic Acid Bacteria Powder 1,000 L of a medium containing 2% glucose and 5% yeast extract was adjusted to pH 6.5 and BPS104 culture obtained by preculture was inoculated thereinto at 1%. While the pH was suitably adjusted, the cells were cultured at 30 to 37° C. for 24 to 48 hours to obtain a cell culture. The resulting cell culture was centrifuged, and 1 part by weight of water was added per part by weight of the cells. Then, the cells were lyophilized, and the solids were pulverized by a pulverizer to obtain 1 kg of lactic acid bacteria BPS104 powder.

Production Example of Lactic Acid Bacteria Capsules 400 g of lactic acid bacteria BPS104 powder and 20 g of sucrose fatty acid ester were mixed. The mixture was filled into hard capsules using a filler to obtain 2,000 capsules of lactic acid bacteria BPS104.

Production Example of Lactic Acid Bacteria Fermented Extract

Example 1

After 1,000 mL of a diluent prepared by diluting royal jelly to a final concentration of 5% was adjusted to pH 6.5, BPS402 culture obtained by preculture was inoculated at 1%. After culture at 30° C. for 48 hours, the residue was removed by centrifugation, and 800 mL of a royal jelly fermented extract was obtained.

Example 2

The same procedure as in Example 1 was repeated to obtain 800 mL of enzyme-treated royal jelly from 1,000 mL of a diluent obtained by diluting enzyme-treated royal jelly fermented extract to a final concentration of 5%.

The fermented extracts obtained in Examples 1 and 2 were tested in the following five items. No effect was indicated as −, and a slight effect was indicated as −/+. Effects were evaluated on a scale of one (+) to three (+++), in ascending order of effects. Table 4 shows the results.

pH Reduction

The fermented extract after 48 hours was evaluated using a pH meter.

Residue Inhibition

The culture after 48 hours was compared with that before fermentation and evaluated.

Viable Cell Maintenance

The culture after 48 hours was suspended. The suspension was suitably diluted, spread-plated onto MRS agar medium, and evaluated.

Melanogenesis Inhibition (i) 20 ml of PBS and 0.2 ml of polyoxyethylene octylphenyl ether (Triton X-100) were mixed and stirred.

(ii) 10 ml of PBS and 19.7 ml of L-DOPA were mixed, and the mixture was wrapped in aluminum foil and stirred.

(iii) 90 μl of (i) and 10 μl of (ii) were added to the fermented extract and B16 melanoma cells (3000 cells/well) cultured for 2 days, and light absorbance (at 490 nm) at 0 and 60 minutes was measured with a microplate reader and evaluated.

Oxidation Inhibition

The color of the medium 5 days after the melanin production inhibition test was confirmed with the naked eye, and oxidation of DOPA was evaluated.

TABLE 4

|  | pH reduction | Residue inhibition | Viable cell maintenance | Melanin production inhibition | Oxidation inhibition |
|---|---|---|---|---|---|
| Example 1 | + | −/+ | + | + | ++ |
| Example 2 | + | ++ | +++ | +++ | + |

Production Example of Lactic Acid Bacteria Fermented Extract Lotion 1,000 mL of a solution containing 0.1% sodium citrate, 1.0% sodium pyrrolidone carboxylate, and 5.0% 1,3-butylene glycol was prepared by mixing each component into purified water at 50° C. 100 mL of ethanol containing 0.6% POE(30)POP(6) decyltetradecyl ether (NIKKOL PEN-4630) was gradually added with stirring to the solution and thereby solubilized. The resulting product was cooled to 30° C. with stirring and the lactic acid bacteria fermented extract obtained in Example 2 was added to a final concentration of 0.5%, thus providing 1,000 mL of a lactic acid bacteria fermented extract lotion.

What is claimed is:

1. A method for:
   (a) overcoming or reducing risk of infection by a pathogen or virus that invades through the respiratory or esophageal mucosa;
   (b) alleviating or reducing risk of food poisoning;
   (c) regulating intestinal function; or
   (d) beautification;
comprising administering to a subject in need thereof *Lactobacillus kunkeei* BPS402 (FERM BP-11439) or treated cells thereof, or *Lactobacillus kunkeei* BPS104 (FERM BP-11438) or treated cells thereof, wherein the administering is effective for overcoming or reducing risk of infection by the pathogen or virus that invades through the respiratory or esophageal mucosa, for alleviating or reducing risk of food poisoning, for regulating intestinal function, or for beautification.

2. The method of claim 1, wherein the administering is effective for overcoming or reducing risk of infection by the pathogen or virus that invades through the respiratory or esophageal mucosa.

3. The method of claim 1, wherein the administering is effective for alleviating or reducing risk of food poisoning.

4. The method of claim 1, wherein the administering is effective for regulating intestinal function.

5. The method of claim 1, wherein the administering is effective for beautification or anti aging.

6. The method of claim 1, wherein the administering is oral.

7. The method of claim 1, wherein the *Lactobacillus kunkeei* BPS402 (FERM BP-11439) or treated cells thereof, or *Lactobacillus kunkeei* BPS104 (FERM BP-11438) or treated cells thereof, are administered in granules.

\* \* \* \* \*

UNITED STATES PATENT AND TRADEMARK OFFICE
CERTIFICATE OF CORRECTION

PATENT NO. : 10,570,366 B2
APPLICATION NO. : 15/835126
DATED : February 25, 2020
INVENTOR(S) : Daisuke Matsuura et al.

Page 1 of 1

It is certified that error appears in the above-identified patent and that said Letters Patent is hereby corrected as shown below:

On the Title Page

Column 1, under Assignee Line 1 – Delete "Company" and insert -- Company, --, therefore.

Column 1, under Assignee Line 2 – After "Okayama" insert -- (JP) --.

Column 2, under Other Publications Line 12 – Delete "infrction" and insert -- infection --, therefore.

In the Claims

Column 22, Line 50 Claim 5 – Delete "beautification or anti aging." and insert -- beautification. --, therefore.

Signed and Sealed this
First Day of September, 2020

Andrei Iancu
*Director of the United States Patent and Trademark Office*